(12) United States Patent
Kwan

(10) Patent No.: US 12,005,093 B2
(45) Date of Patent: Jun. 11, 2024

(54) TRADITIONAL CHINESE MEDICINE EYE DROPS AND THE PREPARATION METHOD THEREOF

(71) Applicant: HONG KONG CHINESE MEDICINE OPHTHALMOLOGY INSTITUTE LIMITED, Hong Kong (CN)

(72) Inventor: See Tung Kwan, Hong Kong (CN)

(73) Assignee: HONG KONG CHINESE MEDICINE OPHTHALMOLOGY INSTITUTE LIMITED, Hong Kong (CN)

( * ) Notice: Subject to any disclaimer, the term of this patent is extended or adjusted under 35 U.S.C. 154(b) by 0 days.

(21) Appl. No.: 17/885,579

(22) Filed: Aug. 11, 2022

(65) Prior Publication Data

US 2024/0050504 A1 Feb. 15, 2024

(51) Int. Cl.

| | |
|---|---|
| *A61K 36/28* | (2006.01) |
| *A61K 9/00* | (2006.01) |
| *A61K 31/235* | (2006.01) |
| *A61K 35/413* | (2015.01) |
| *A61K 36/25* | (2006.01) |
| *A61K 36/286* | (2006.01) |
| *A61K 36/533* | (2006.01) |
| *A61K 36/59* | (2006.01) |
| *A61K 36/808* | (2006.01) |
| *A61K 47/02* | (2006.01) |

(52) U.S. Cl.
CPC ............ *A61K 36/28* (2013.01); *A61K 9/0048* (2013.01); *A61K 31/235* (2013.01); *A61K 35/413* (2013.01); *A61K 36/25* (2013.01); *A61K 36/286* (2013.01); *A61K 36/533* (2013.01); *A61K 36/59* (2013.01); *A61K 36/808* (2013.01); *A61K 47/02* (2013.01); *A61K 2236/331* (2013.01); *A61K 2236/39* (2013.01); *A61K 2236/53* (2013.01)

(58) Field of Classification Search
None
See application file for complete search history.

(56) References Cited

U.S. PATENT DOCUMENTS

| | | | | |
|---|---|---|---|---|
| 5,804,597 | A | * | 9/1998 | Yamakoshi ............. A61P 27/02 514/456 |
| 2003/0124112 | A1 | * | 7/2003 | Molnarne-Kahan ......................... A61K 9/0048 514/397 |
| 2004/0001896 | A1 | * | 1/2004 | Kuppam ................. A61P 27/06 424/769 |
| 2005/0065091 | A1 | * | 3/2005 | Peyman ............... A61K 31/375 514/474 |

FOREIGN PATENT DOCUMENTS

| | | | | |
|---|---|---|---|---|
| CN | 103638432 | A | * | 3/2014 |
| CN | 107432909 | A | * | 12/2017 ............... A23F 3/34 |

* cited by examiner

*Primary Examiner* — Aaron J Kosar
*Assistant Examiner* — Jacob A Boeckelman

(57) ABSTRACT

The present invention relates to the preparation technical field of traditional Chinese medicine and more particularly, to a traditional Chinese medicine eye drops and the preparation method thereof. The traditional Chinese medicine components of the traditional Chinese medicine eye drops provided by the embodiments of the invention comprise: ginseng *Radix* et rhizoma of 5-10 wt %, scrophulariae *Radix* of 15-20 wt %, xanthii *Fructus* of 5-10 wt %, bovis *Calculus* sativus of 5-10 wt %, Carthami *flos* of 5-10 wt %, borneolum of 5-10 wt %, senecionis scandentis *herba* of 25-35 wt %, fibraureae *caulis* of 5-15 wt % and motherwort fruit of 5-10 wt %.

3 Claims, 2 Drawing Sheets

TRADITIONAL CHINESE MEDICINE EYE DROPS AND THE PREPARATION METHOD THEREOF

TECHNICAL FIELD

The present invention relates to the preparation technical field of traditional Chinese medicine and more particularly, to a traditional Chinese medicine eye drops and the preparation method thereof.

BACKGROUND

Eyes are one of the most important organs of human beings, providing a guarantee for people to adapt to social life. People who lose the vision will lead a boring and miserable life. Acquired blindness accounts for ninety percent of the blind, due to various chronic eye diseases which have not been timely and thoroughly treated.

With the acceleration of the pace of life, there raises the utilization of mobile phones, computers and other electronic products, and the incidence of eye diseases including eye discomfort, eye fatigue and dry eyes is also increasing. Eye drops is one of the most commonly used pharmaceutical dosage forms for eye diseases, with a fast and direct acting on most eye diseases. In terms of the traditional Chinese medicine, besides decoction as the most commonly used pharmaceutical dosage forms, there are also pills, powder, ointment and bolus which are used in prevention and treatment of human's disease for thousands of years.

In the process of exploiting the invention, the inventor finds that in the relevant technology, most topical eye drops to treat eye diseases adopts western medicine components, which have large stimulation to eyes and will bring large side effects while treating eye diseases. The traditional Chinese medicine eye drops on the market, however, is mostly health care type eye drops, which is able to relieve various symptoms caused by eye fatigue, but do not have therapeutic effect.

DESCRIPTION OF THE INVENTION

In order to play the special role of the traditional Chinese medicine in the treatment of human eye diseases, a traditional Chinese medicine eye drops and the preparation method thereof provided by the embodiments of the invention, are able to make a traditional Chinese medicine eye drops to treat eye diseases using the traditional Chinese medicine components including ginseng Radix et rhizoma, scrophulariae Radix, xanthii Fructus, bovis Calculus sativus, Carthami flos, borneolum, senecionis scandentis herba, fibraureae caulis and motherwort fruit.

To resolve above technical problems, technical solutions provided by the embodiments of the invention comprise:

First, the embodiments of the invention provide a traditional Chinese medicine eye drops, which is made of traditional Chinese medicine components and pharmaceutical necessities. In terms of weight percentage, the said traditional Chinese medicine components comprise:

Ginseng Radix et rhizoma of 5-10 wt %, scrophulariae Radix of 15-20 wt %, xanthii Fructus of 5-10 wt %, bovis Calculus sativus of 5-10 wt %, Carthami flos of 5-10 wt %, borneolum of 5-10 wt %, senecionis scandentis herba of 25-35 wt %, fibraureae caulis of 5-15 wt % and motherwort fruit of 5-10 wt %.

Alternatively, in terms of weight percentage, the said traditional Chinese medicine components comprise:

the said ginseng Radix et rhizoma of 7.5 wt %, the said scrophulariae Radix of 15 wt %, the said xanthii Fructus of 7.5 wt %, the said bovis Calculus sativus of 7.5 wt %, the said Carthami flos of 7.5 wt %, the said natural borneolum of 7.5 wt %, the said senecionis scandentis herba of 30 wt %, the said fibraureae caulis of 10 wt % and the said motherwort fruit of 7.5 wt %;

Alternatively, the said pharmaceutical necessities comprise purified water, sodium chloride injection and pH regulator;

Alternatively, the said pharmaceutical necessities further comprise antiseptics.

Alternatively, the said pH regulator comprises boric acid, and the said antiseptics comprise ethylparaben, and/or the mass ratio of the said pH regulator and the said antiseptics is 1:1;

Alternatively, pH value of the said traditional Chinese medicine eye drops is 5-9;

Second, the embodiments of the invention further provide a preparation method of a traditional Chinese medicine eye drops, which is characterized in that, the said methods comprise:

Ginseng Radix et rhizoma of 5-10 wt %, scrophulariae Radix of 15-20 wt %, xanthii Fructus of 5-10 wt %, Carthami flos of 5-10 wt %, senecionis scandentis herba of 25-35 wt %, fibraureae caulis of 5-15 wt % and motherwort fruit of 5-10 wt % of the traditional Chinese medicine components are added into the purified water, decocted and filtered, to obtain the first extract;

Sodium chloride injection is added into purified water, heated and boiled. After cooled to 70-90° C., the solution is added with the first extract, and further cooled to 50-70° C., to obtain the first mixture;

The said bovis Calculus sativus of 5-10 wt % and natural borneolum of 5-10 wt % are heated and reflow with ethanol, and filtered to obtain the second extract;

After dropping the said second extract into the said first mixture, antiseptics and purified water are added to preliminarily prepare the traditional Chinese medicine eye drops;

Alternatively, after dropping the said second extract into the said first mixture, antiseptics and purified water are added to preliminarily prepare the traditional Chinese medicine eye drops, and the said methods further comprise:

Measure the pH value of the said traditional Chinese medicine eye drops;

Adjust the pH value of the traditional Chinese medicine eye drops by the pH regulator, if the measured pH value is beyond the preset range.

Alternatively, the said pH regulator comprises boric acid, and the said antiseptics comprise ethylparaben;

Alternatively, during the preparation of the said first extract, the mass ratio of the total mass of the said ginseng Radix et rhizoma, the said scrophulariae Radix, the said xanthii Fructus, the said Carthami flos, the said senecionis scandentis herba, the said fibraureae caulis and the said motherwort fruit to the purified water is 1:20.

The benefits of the embodiments of the invention are: distinguished from the existing techniques, the present embodiments of the invention provide a traditional Chinese medicine eye drops and the preparation method thereof, and the traditional Chinese medicine eye drops is made of traditional Chinese medicine components and pharmaceutical necessities. In terms of weight percentage, the traditional Chinese medicine components comprise: ginseng *Radix* et rhizoma of 5-10 wt %, scrophulariae *Radix* of 15-20 wt %, *xanthii fructus* of 5-10 wt %, bovis *Calculus sativus* of 5-10 wt %, *Carthami flos* of 5-10 wt %, borneolum of 5-10 wt %, *senecionis* scandentis *herba* of 25-35 wt %, fibraureae *caulis* of 5-15 wt % and motherwort fruit of 5-10 wt %. The traditional Chinese medicine eye drops provided by the embodiments of the invention is able to remove nebula to improve vision, clear heat and detoxicate, promote blood circulation to remove meridian obstruction, remove stagnation and relieve pain through the above components. The traditional Chinese medicine eye drops shows well curative effects on wind-fire red eye (also known as pinkeye, characterized by hot eyes, conjunctive congestion with swelling and pain, photodysphoria, lacrimation induced by irritation of the wind, and itch and dry eyes), cataract (characterized by leukoma barrier in pupils, blurred vision and vitreous opacitees at the beginning and furthermore blindness) and glaucoma (characterized by dim-sighted eyes, swelling and pain of eyes, headache, and nausea and vomiting), diabetic maculopathy (characterized by metamorphopsia, blurred vision with shadow, and diminution of vision) and myopia (such as mild juvenile myopia characterized by clear near vision and blurred distant vision).

DESCRIPTION OF THE DRAWINGS

The drawings required in the embodiments of the invention are briefly introduced to more clearly state the technical solutions of the embodiments of the invention. It is obvious that the drawings described hereunder are only some embodiments of the invention, from which other drawings may also be obtained without creative effort by those of ordinary skill in the art.

DETAILED DESCRIPTION OF THE EMBODIMENTS

Figure 1:
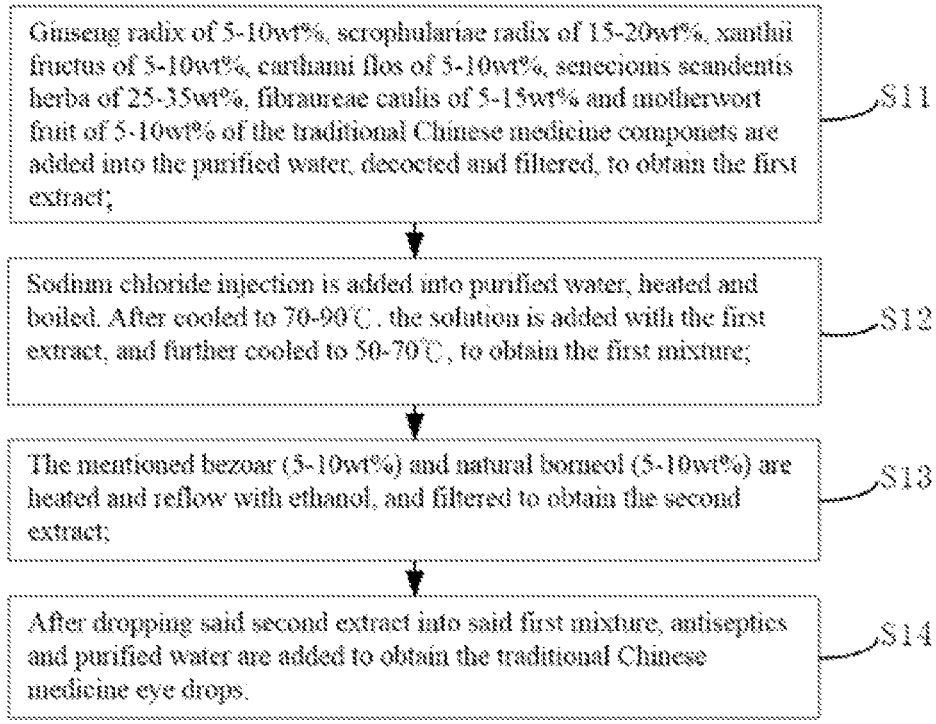
FIG. 1 is a schematic diagram of the preparation process of traditional Chinese medicine eye drops provided by an embodiment of the invention.
Figure 2:
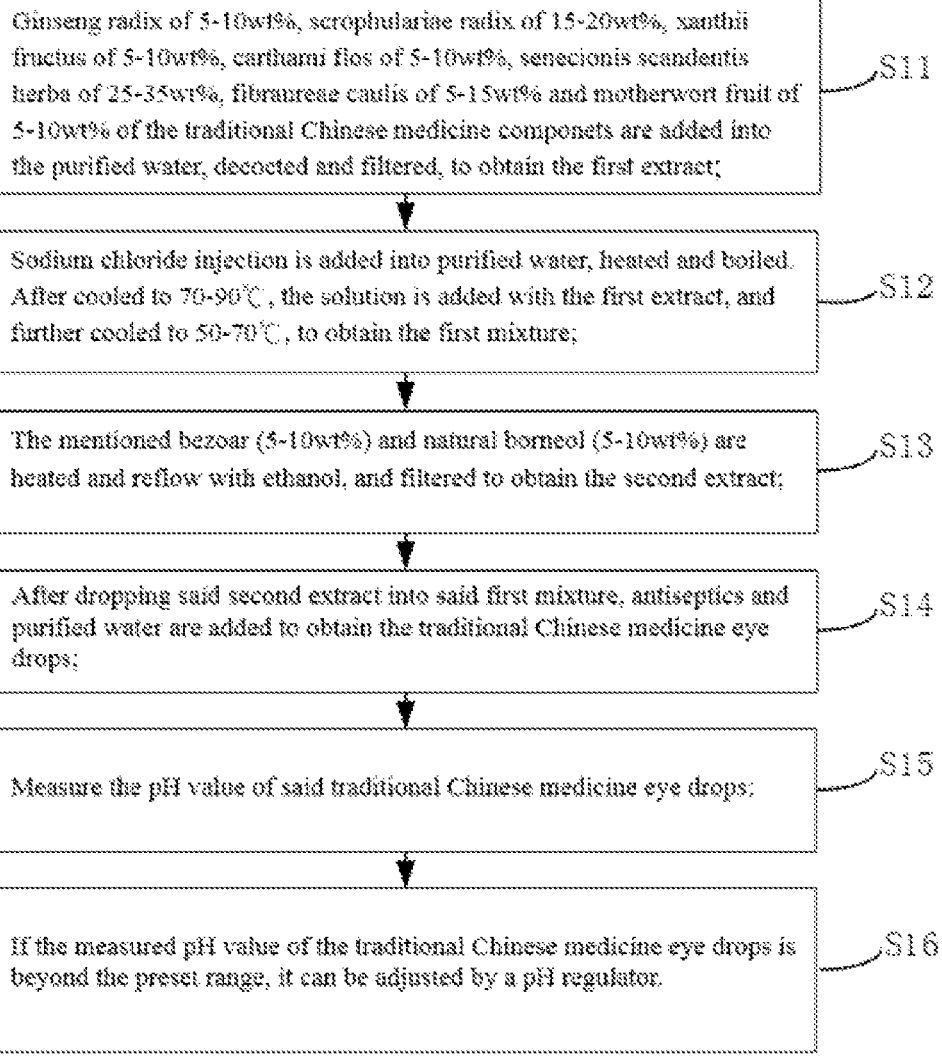
FIG. 2 is a schematic diagram of the preparation process of traditional Chinese medicine eye drops provided by another embodiment of the invention.

In order to make the objectives, technical solutions and advantages of the present invention clearer, the present invention will be further described in detail below with reference to the accompanying drawings and embodiments. It should be understood that the specific embodiments described herein are only used to explain the present invention, but not to limit the present invention.

It should be noted that, if there is no conflict, the invention comprises all of the combinations of the features in the embodiments of the invention. In addition, although the functional modules in the device diagram are divided and the logical order is shown in the flowchart, in some cases the steps shown or described may be performed in a different functional module division or in a different order.

Unless otherwise specified, all technical and scientific terms used in this specification have the same meaning as commonly understood by those skilled in the technical field of the invention. The terms used in this specification of the invention are only for the purpose of describing specific embodiments and are not intended to limit the invention. The terms and/or in this specification comprise arbitrary and all combinations of one or more related listed items.

The embodiments of the invention provide a traditional Chinese medicine eye drops, which is made of traditional Chinese medicine components and pharmaceutical necessities. In terms of weight percentage, the traditional Chinese medicine components comprise: ginseng *Radix* et rhizoma of 5-10 wt %, scrophulariae *Radix* of 15-20 wt %, *xanthii Fructus* of 5-10 wt %, bovis *Calculus sativus* of 5-10 wt %, *Carthami flos* of 5-10 wt %, borneolum of 5-10 wt %, *senecionis* scandentis *herba* of 25-35 wt %, fibraureae *caulis* of 5-15 wt % and motherwort fruit of 5-10 wt %.

To achieve better curative effects, in some embodiments, in terms of weight percentage, the traditional Chinese medicine components comprise the said ginseng *Radix* et rhizoma of 7.5 wt %, the said scrophulariae *Radix* of 15 wt %, the said *xanthii Fructus* of 7.5 wt %, the said bovis *Calculus sativus* of 7.5 wt %, the said *Carthami flos* of 7.5 wt %, the said natural borneolum of 7.5 wt %, the said *senecionis* scandentis *herba* of 30 wt %, the said fibraureae *caulis* of 10 wt % and the said motherwort fruit of 7.5 wt %;

In some embodiments, pharmaceutical necessities comprise purified water, sodium chloride injection and pH regulator; Pharmaceutical necessities may further comprise antiseptics and pH regulator, wherein the mass ratio of the said pH regulator and the said antiseptics is 1:1; The said pH regulator comprises boric acid, and the said antiseptics which comprise ethylparaben; pH regulator is used to adjust the pH value of the traditional Chinese medicine eye drops to 5-9.

Traditional Chinese medicine believes that the wind is light and upward and the heat-evil is also upward, so the wind-evil and heat-evil are accumulated in the eyes and causes eye diseases including hot eyes, conjunctive congestion with swelling and pain, photodysphoria, or red and swollen eyelids and edema of white of the eyes; if the heat-evil hastens blood flow and the blood overflow, there appears dotted or patchy hemorrhage in the white of the eyes; and as for the heat, headache, dry mouth, bitter mouth, dark urine and dry stool, red tongue and moss yellow, wiry pulse or multiple pulse are all wind-evil and heat-evil syndromes. Preferred treatments comprise clearing heat and detoxification, dispelling the itching caused by the wind-evil, and relieving the redness of the eyes and improving acuity of vision.

The book "*Mujing Dacheng*" says: cataract refers to the disease characterized by blindness without diseases, and cataract over the intraocular fluid in the pupils. The book "*Treatise on Seventy-two Recipes of Michuan Yanke Longmu Lun*" says: in terms of cataract, patients with early stage of illness appear myiodesopsia, and have a blurred vision as covered by smoke, which is gradually aggravated, neither pain nor itching, and finally become blind. Also says: manifestations of cataract are like the water frozen on the eyes, with the pupils overshadowed by the white surface nebula. It suggests that the primary symptoms of cataract are while nebula covering the pupils, and blurred vision and even blindness.

The book "*Chapter Two of Michuan Yanke Longmu Lun*" says: in terms of glaucoma, patients with early stage of illness appear migraine in the head and forehead, and also palpebral and nasofrontal bone pain, and have ophthalmodynia and blurred vision. The disease often attacks in one eye at first, after vomiting and nausea, or hiccup. It suggests that the manifestations of glaucoma include blurred vision, headache, ophthalmodynia, vomiting and nausea, and the disease often attack in one eye at first.

The pathogenesis of diabetes mainly lies in the deficiency of Yin and body fluid and the excess of dry heat. Yin deficiency is the root cause while dry heat is the symptom, which are reciprocal causation. The deficiency of Yin increases the excess of dry heat, and the excess of dry heat increases the deficiency of Yin. If diabetes lasts for a long time, dry heat evil will damage the blood vessels in the eyes, which become abnormal. Yin deficiency, dry heat, and blood stasis, as well as Qi deficiency, are the main pathogenesis of diabetic eye diseases.

Myopia is often caused due to improper use of eyes at work or during study of teenagers, or an inadequate natural endowment or congenital genetic cause. The pathogenesis of the disease is mainly deficiency of heart Yang, and vision is unable to reach far; or the pathogenesis of the disease may be the liver and kidney deficiency and insufficient blood, which cause poor vision that is unable to reach far. This prescription is designed for the head and eyes with insufficient blood and essence support due to the deficiency of liver and kidney caused by deficiency of congenital endowment, or for the eyes with insufficient blood and Qi support due to exhaustion of Qi and blood caused by overuse of eyes during use of electronic devices by teenagers.

In the prescription, *senecionis* scandentis *herba*, natural borneolum (dextral borneolum), and scrophulariae *Radix* are used as monarch drug; therein *senecionis* scandentis *herba*, which is bitter in taste and cold in nature, with the effect of clearing heat and detoxification, removing pathogenic heat from blood, and relieving swelling, clearing liver and improving vision, is a commonly used Chinese herb in ophthalmology to treat wind-fire red eye and nebula. The book "*Baicao Jing*" says: *senecionis* scandentis *herba* treats blurred vision, redness and cataract, and lacrimation induced by irritation of the wind. Scrophulariae *Radix* are able to clear heat and cool blood, nourish Yin and reduce fire, which is good at treating dry and blurred eyes. The book "*Sheng Nong's herbal classic*" says: scrophulariae *Radix* are able to tonify kidney Qi and improve vision. The book "*Intergrating Chinese and Western Medicine*" says: further explains that why scrophulariae *Radix* are able to improve the vision is because that the liver acts on the eyes, and the scrophulariae *Radix* are able to nourish the liver, so to clear the eyes and improve the vision. Moreover, eyes are able to see things is due to the sufficient fluid in the pupils which is the appearance of the kidney essence. Natural borneolum (dextral borneolum) is spicy in taste and fragrant in nature, which is able to unblock the apertures in the human head and remove heat, remove cataract and improve vision, relieve swelling and pain. The book "*Bencao Jingshu*" says: eyes with redness is caused by heat-evil; and borneolum is spicy in taste and warm in nature, with dispersing actions, able to lead the elimination of fire and heat Qi, resulting in improvement of vision, and elimination of redness, pain and nebula in eyes, which is good at treating various internal and external obstacles. The book "*Haiyao Bencao*" says: the major function of borneolum is to treat internal and external obstacles and improve vision. So, the combination of the three drugs is able to increase the curative effects of removing heat from blood, nourishing Yin and improving vision.

The liver opens at the eyes. *Bovis Calculus sativus*, bitter in taste and cool in nature, enters into the heart and liver meridian, is able to cool the liver and relieve wind, and clear heat and detoxification. There is a common saying that the itching is caused by the wind-evil, and to treat wind-evil one should treat blood at first, so the wind would be eliminated if blood moves smooth. Therefore, *Carthami flos* and motherwort fruit are added to promote circulation, wherein *Carthami flos* is able to harmonize the blood and relieve pain, and motherwort fruit, which is able to dispel wind-evil, clear heat-evil, tonify essence and improve vision; The book "*Sheng Nong's herbal classic*" says: *Carthami flos* is able to treat redness, swelling, pain and nebula in eyes, the two drugs are used as minister drug.

Fibraureae *caulis*, also known as rhizoma coptidis, bitter in taste and cold in nature, is able to enter into the heart and liver meridian clear the heat-evil and detoxification, and be good at treating red eye. The book "*Yinhai Jingwei* (a profound treatise on eye diseases)" says: red eye is characterized by redness of eyes and pains in eyes. Fibraureae *caulis* is used as an assistant drug.

*Ginseng Radix* et rhizoma tonifies vitality, which is able to assist the dispersing actions of natural borneolum (dextral borneolum) without consumption of Qi, is used as a conductant drug.

The traditional Chinese medicine eye drops provided by the embodiments of the invention is able to play a curative effect of removing nebula to improve vision, clearing heat and detoxification, promoting blood circulation to remove meridian obstruction, removing stagnation and relieving pain through the combination of *ginseng Radix* et rhizoma, scrophulariae *Radix*, *xanthii Fructus*, *bovis Calculus sativus*, *Carthami flos*, natural borneolum, *senecionis* scandentis *herba*, fibraureae *caulis* and motherwort fruit. The traditional Chinese medicine eye drops is mainly used for wind-fire red eye (also known as pinkeye, characterized by hot eyes, conjunctival congestion with swelling and pain, photodysphoria, lacrimation induced by irritation of the wind, and itch and dry eyes), cataract (characterized by leukoma barrier in pupils, blurred vision and vitreous opacitees at the beginning and furthermore blindness) and glaucoma (characterized by dim-sighted eyes, swelling and pain of eyes, headache, and nausea and vomiting), diabetic maculopathy (characterized by metamorphopsia, blurred vision with shadow, and diminution of vision) and myopia (such as mild juvenile myopia characterized by clear near vision and blurred distant vision).

Usage and dosage of the traditional Chinese medicine eye drops provided by the embodiments of the invention is 2-3 drops every time, and 2-3 times every day.

The embodiments of the invention further provide a preparation method of a traditional Chinese medicine eye drops. FIG. 1 is a schematic diagram of the preparation process of traditional Chinese medicine eye drops. The methods as shown in FIG. 1 comprise the following steps:

S11, *ginseng Radix* et rhizoma of 5-10 wt %, scrophulariae *Radix* of 15-20 wt %, *xanthii Fructus* of 5-10 wt %, *Carthami flos* of 5-10 wt %, *senecionis* scandentis *herba* of 25-35 wt %, fibraureae *caulis* of 5-15 wt % and motherwort fruit of 5-10 wt % of the traditional Chinese medicine components are added into the purified water, decocted and filtered, to obtain the first extract;

In this embodiment, *ginseng Radix* et rhizoma of 5-10 wt %, scrophulariae *Radix* of 15-20 wt %, *xanthii Fructus* of 5-10 wt %, *Carthami Flos* of 5-10 wt %, *senecionis* scandentis *herba* of 25-35 wt %, fibraureae *caulis* of 5-15 wt % and motherwort fruit of 5-10 wt % of the traditional Chinese medicine components are mixed, crushed, sieved and re-mixed, and added into the purified water with the amount 20 times of the mixture to decocte for 2 times, 1 hour each time; the traditional Chinese medicine decoction is concentrated to proper volume through decompressing concentration and is left to steady state, then the supernatant is taken for suction filtration to obtain the first extract;

S12, sodium chloride injection is added into purified water, heated and boiled. After cooled to 70-90° C., the solution is added with the first extract, and further cooled to 50-70° C., to obtain the first mixture;

Sodium chloride injection is added into proper purified water, heated and boiled. After cooled to 70-90° C., the solution is added with the first extract, and further stirred and cooled to 50-70° C.;

S13, the said *bovis Calculus sativus* (5-10 wt %) and natural borneolum (5-10 wt %) are heated and reflow with ethanol, and filtered to obtain the second extract;

*Bovis Calculus sativus* and natural borneolum are heated and reflow with ethanol for half an hour, the ethanol is recycled till no alcohol taste and then filtered, the filtrate is in stock;

S14, after dropping the said second extract into the said first mixture, antiseptics and purified water are added to obtain the traditional Chinese medicine eye drops;

After dropping the said extract into the said solution while agitation, ethylparaben (antiseptics) and purified water are added and stirred for above 30 minutes.

Alternatively, in some embodiments, the above methods further comprise the following steps:

S15, measure the pH value of the said traditional Chinese medicine eye drops;

S16, adjust the pH value of the traditional Chinese medicine eye drops by the pH regulator, if the measured pH value is beyond the preset range;

Measure the pH value of the solution. If the measured pH value of the traditional Chinese medicine eye drops is beyond the preset range, according to the required pH value of traditional Chinese medicine eye drops, an appropriate amount of boric acid is added to adjust the pH value of the solution to the predetermined range. The predetermined range of pH value may be 5-9. After that, the solution is filtered and sterilized to obtain the final product of traditional Chinese medicine eye drops.

Specifically, in some embodiments, ginseng *Radix* et rhizoma of 1.5 g, scrophulariae *Radix* of 3 g, *xanthii fructus* of 1.5 g, *Carthami flos* of 1.5 g, *senecionis* scandentis *herba* of 1.5 g, fibraureae *caulis* of 2 g and motherwort fruit of 1.5 g are mixed, crushed, sieved and re-mixed, and added with 340 ml purified water and decocted for 2 times, 1 hour each time. The decoction is concentrated to proper volume through decompressing concentration and is left to steady state, then the supernatant is taken in stock. A total of 15 g sodium chloride injection is added into purified water, heated and boiled. After cooled to 80° C., the solution is added with the first extract, and further cooled to 60° C. while stirring. A total of 1.5 g *bovis Calculus sativus* and 1.5 g natural borneolum (dextral borneolum) are heated and reflow with 175 g ethanol for half an hour; the ethanol is recycled till no alcohol taste and then filtered, the filtrate is in stock; After dropping the said extract into the said solution while agitation, 0.25 g ethylparaben (antiseptics) is added, and purified water is added to a total volume of 1000 ml. The solution is stirred for above 30 minutes and the pH value is measured. According to the required pH value of the final product, 0.25 g boric acid is added if necessary. The pH value of the solution is adjusted to the range of pH 5-9 (according to the pH test method of Chinese Pharmacopoeia [Appendix VII G]). The solution is filtered, and the filtrate is sterilized and sealed to obtain the final product of traditional Chinese medicine eye drops.

Embodiment 1

Preparation process of a traditional Chinese medicine eye drops provided by this embodiment of the invention is as follow:

Ginseng *Radix* et rhizoma of 7.5 wt %, scrophulariae *Radix* of 15 wt %, *xanthii Fructus* of 7.5 wt %, *Carthami flos* of 7.5 wt %, natural borneolum of 7.5 wt %, *senecionis* scandentis *herba* of 30 wt %, fibraureae *caulis* of 10 wt % and motherwort fruit of 7.5 wt % of the traditional Chinese medicine components are added into the purified water, decocted and filtered, to obtain the first extract;

Sodium chloride injection is added into purified water, heated and boiled. After cooled to 80° C., the solution is added with the first extract, and further cooled to 60° C., to obtain the first mixture;

The said *bovis Calculus sativus* of 7.5 wt % and natural borneolum of 7.5 wt % are heated and reflow with ethanol, and filtered to obtain the second extract;

After dropping the said second extract into the said first mixture, ethylparaben and purified water are added to preliminarily prepare the traditional Chinese medicine eye drops;

pH value of the traditional Chinese medicine eye drops is measured and adjusted by boric acid to 9;

Embodiment 2

Preparation process of a traditional Chinese medicine eye drops provided by this embodiment of the invention.

Ginseng *Radix* et rhizoma of 10 wt %, scrophulariae *Radix* of 15 wt %, *xanthii Fructus* of 5 wt %, *Carthami flos* of 5 wt %, *senecionis* scandentis *herba* of 35 wt %, fibraureae *caulis* of 5 wt % and motherwort fruit of 5 wt % of the traditional Chinese medicine components are added into the purified water, decocted and filtered, to obtain the first extract;

Sodium chloride injection is added into purified water, heated and boiled. After cooled to 80° C., the solution is added with the first extract, and further cooled to 60° C., to obtain the first mixture;

The said *bovis Calculus sativus* of 10 wt % and natural borneolum of 10 wt % are heated and reflow with ethanol, and filtered to obtain the second extract;

After dropping the said second extract into the said first mixture, ethylparaben and purified water are added to preliminarily prepare the traditional Chinese medicine eye drops;

pH value of the traditional Chinese medicine eye drops is measured and adjusted by boric acid to 6;

Embodiment 3

Preparation process of a traditional Chinese medicine eye drops provided by this embodiment of the invention.

Ginseng *Radix* et rhizoma of 10 wt %, scrophulariae *Radix* of 20 wt %, *xanthii Fructus* of 5 wt %, *Carthami flos* of 5 wt %, *senecionis* scandentis *herba* of 35 wt %, fibraureae *caulis* of 5 wt % and motherwort fruit of 5 wt % of the traditional Chinese medicine components are added into the purified water, decocted and filtered, to obtain the first extract;

Sodium chloride injection is added into purified water, heated and boiled. After cooled to 80° C., the solution is added with the first extract, and further cooled to 50° C., to obtain the first mixture;

The said *bovis Calculus sativus* of 5 wt % and natural borneolum of 10 wt % are heated and reflow with ethanol, and filtered to obtain the second extract;

After dropping the said second extract into the said first mixture, ethylparaben and purified water are added to preliminarily prepare the traditional Chinese medicine eye drops;

pH value of the traditional Chinese medicine eye drops is measured and adjusted by boric acid to 5;

Test:

The traditional Chinese medicine eye drops in Embodiments 1-3 are carried out in the following clinical trials:

1. Experimental Subjects and Materials

The observation subjects including a total of 36 patients with clinically confirmed eye disease, both male and female, aging from 5 years to 66 years, with an average age of 30 years.

All the patients are divided into three groups, naming Group 1-3, with 12 cases in each group. Statistics software SPSS is used to compare the age and symptom scores of three groups. $P>0.05$ indicates no statistically significant differences, namely the three groups are comparable.

2. Selection Criteria of Subjects 2.1 Inclusion criteria (1) Clinically confirmed eye diseases;

(2) Aging from 5 to 75 years;

(3) Signed informed consent.

2.2 Exclusion criteria (1) History of allergy;

(2) Diseases of other organs.

3. Experimental Methods

Patients with eye disease in Group 1 are treated with the traditional Chinese medicine eye drops prepared by the method in Embodiment 1, and patients in Groups 2 and 3 are treated with the traditional Chinese medicine eye drops prepared by the method in Embodiments 2 and 3, respectively; Patients of all three groups are given 2-3 drops each time, 2-3 times every day, and their physical reactions are examined and recorded.

4. Evaluation Standards on Curative Effect of Traditional Chinese Medicine Syndrome The syndromes including hot eyes, conjunctive congestion with swelling and pain, photodysphoria, lacrimation induced by irritation of the wind, and itch and dry eyes, leukoma barrier in pupils, blurred vision, diminution of vision, vitreous opacitees, swelling and pain of eyes, glaucoma and headache are divided into three levels, namely asymptomatic, mild and severe level, with the corresponding score of 0, 2, 4 points. The subjects are scored after 20 days of treatments.

Efficacy index$(n)$=[(baseline scores−scores after treatments)/baseline scores]*100%

Marked: refers to that most of the said symptoms are disappeared, and the effective rate $n≥70%$;

Valid: refers to that the said symptoms are basically disappeared, and the effective rate $30% ≤ n < 70%$;

Invalid: refers to that the said symptoms are improved to certain degree, and the effective rate $n<30%$;

The effective rate=[number of marked cases+number of valid cases/number of total cases]*100%

5. Experimental Results

TABLE 1

Results of clinical trails

| Groups | Marked cases | Valid cases | Invalid cases | Effective rate (%) |
|---|---|---|---|---|
| 1 | 7 | 4 | 1 | 92.66 |
| 2 | 5 | 5 | 2 | 84.35 |
| 3 | 8 | 2 | 2 | 84.35 |

From the results of Tab.1, the traditional Chinese medicine eye drops provided by an embodiment of the invention has good curative effects on the syndromes including hot eyes, conjunctive congestion with swelling and pain, photodysphoria, lacrimation induced by irritation of the wind, and itch and dry eyes, leukoma barrier in pupils, blurred vision, diminution of vision, vitreous opacitees, swelling and pain of eyes, glaucoma and headache. And the effective rate is as high as 92.66%.

In conclusion, the said eye drops has at least the following benefits:

The said eye drops is able to remove nebula to improve vision, clear heat and detoxicate, promote blood circulation to remove meridian obstruction, remove stagnation and relieve pain, showing well curative effects on wind-fire red eye (also known as pinkeye, characterized by hot eyes, conjunctive congestion with swelling and pain, photodysphoria, lacrimation induced by irritation of the wind, and itch and dry eyes), cataract (characterized by leukoma barrier in pupils, blurred vision and vitreous opacitees at the beginning and furthermore blindness) and glaucoma (characterized by dim-sighted eyes, swelling and pain of eyes, headache, and nausea and vomiting), diabetic maculopathy (characterized by metamorphopsia, blurred vision with shadow, and diminution of vision) and myopia (such as mild juvenile myopia characterized by clear near vision and blurred distant vision).

Finally, it should be noted that: the above embodiments are only used to illustrate the technical solutions of the invention, but not to limit the invention; Under the thought of the invention, the technical features in the above embodiments or in different embodiments may be combined, and the steps may be realized in any order, and there are many other variations of the different aspects of the above-described invention, which are not provided in detail for the sake of brevity; Although the detailed description of the invention with reference to the foregoing embodiments, those of ordinary skill in the art should understand that: they may modify the technical solutions recorded in the foregoing embodiments or make equivalent substitutions for some of the technical features thereof; Such modification or substitution shall not make the essence of the corresponding technical solutions deviate from the scope of the technical solutions of each embodiment of the invention.

What is claimed is:

1. A traditional Chinese medicine eye drops, which is characterized in that, the traditional Chinese medicine eye drops is made of traditional Chinese medicine components and pharmaceutical necessities, by weight percentage, wherein the components comprise: *ginseng Radix* et rhizoma of 5-10 wt %, scrophulariae *Radix* of 15-20 wt %, *xanthii Fructus* of 5-10 wt %, *bovis Calculus sativus* of 5-10 wt %, *Carthami flos* of 5-10 wt %, borneolum of 5-10 wt %, *senecionis* scandentis *herba* of 25-35 wt %, fibraureae *caulis* of 5-15 wt % and motherwort fruit of 5-10 wt %; wherein the said pharmaceutical necessities consists of: purified water, sodium chloride injection and pH regulator, wherein the pH value of the said traditional Chinese medicine eye drop is 5-9.

2. The traditional Chinese medicine eye drops according to claim 1, which is characterized in that, in terms of weight percentage, the components comprise:

the said *ginseng Radix* et rhizoma of 7.5 wt %, the said scrophulariae *Radix* of 15 wt %, the said *xanthii Fructus* of 7.5 wt %, the said *bovis Calculus sativus* of 7.5 wt %, the said *Carthami flos* of 7.5 wt %, the said natural borneolum of 7.5 wt %, the said *senecionis scandentis herba* of 30 wt %, the said fibraureae *caulis* of 10 wt % and the said motherwort fruit of 7.5 wt %.

3. The traditional Chinese medicine eye drops according to claim 1, which is characterized in that, the said pH regulator comprises boric acid, and the said antiseptics comprise ethylparaben, and/or the mass ratio of the said pH regulator and the said antiseptics is 1:1.

* * * * *